(12) United States Patent
Gombart et al.

(10) Patent No.: US 9,526,685 B2
(45) Date of Patent: Dec. 27, 2016

(54) COSMETIC CARE COMPOSITION AND METHOD USING AN ELASTIC MIXTURE

(71) Applicant: LVMH RECHERCHE, Saint Jean de Braye (FR)

(72) Inventors: Emilie Gombart, Orleans (FR); Jean-Francois Tranchant, Marigny les Usages (FR); Alex Poulin, Jargeau (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 116 days.

(21) Appl. No.: 14/399,717

(22) PCT Filed: May 6, 2013

(86) PCT No.: PCT/FR2013/051005
§ 371 (c)(1),
(2) Date: Nov. 7, 2014

(87) PCT Pub. No.: WO2013/167835
PCT Pub. Date: Nov. 14, 2013

(65) Prior Publication Data
US 2015/0132247 A1      May 14, 2015

(30) Foreign Application Priority Data
May 10, 2012    (FR) ..................... 12 54269

(51) Int. Cl.
| A61K 8/81 | (2006.01) |
|---|---|
| A61K 8/73 | (2006.01) |
| A61Q 19/08 | (2006.01) |
| A61K 8/34 | (2006.01) |
| A61Q 19/00 | (2006.01) |

(52) U.S. Cl.
CPC ............. *A61K 8/8129* (2013.01); *A61K 8/345* (2013.01); *A61K 8/731* (2013.01); *A61K 8/732* (2013.01); *A61K 8/8117* (2013.01); *A61K 8/8176* (2013.01); *A61K 8/8182* (2013.01); *A61Q 19/00* (2013.01); *A61Q 19/08* (2013.01); *A61K 2800/48* (2013.01); *A61K 2800/594* (2013.01)

(58) Field of Classification Search
CPC .... A61K 8/731; A61K 8/8129; A61K 8/8176; A61K 8/345
USPC ........................................... 424/78.03
See application file for complete search history.

(56) References Cited

U.S. PATENT DOCUMENTS

| 6,440,432 B1 | 8/2002 | Mukherjee et al. | |
|---|---|---|---|
| 2002/0018793 A1* | 2/2002 | Mochizuki | A61K 8/0212 424/402 |
| 2005/0184427 A1* | 8/2005 | Yang | A61K 9/006 264/175 |
| 2008/0081055 A1 | 4/2008 | Cassin | |
| 2010/0021399 A1 | 1/2010 | Rampoldi et al. | |
| 2010/0021404 A1 | 1/2010 | Delage-Grouiller et al. | |

FOREIGN PATENT DOCUMENTS

| EP | 0970681 | 1/2000 |
|---|---|---|
| EP | 1892015 | 2/2008 |
| WO | WO 00/56270 | 9/2000 |
| WO | WO 03/017967 | 3/2003 |
| WO | WO 03/030882 | 4/2003 |
| WO | WO 2008/012220 | 1/2008 |

OTHER PUBLICATIONS

"Monograph ID 115: Aluminum Starch Octenylsuccinate"; International Cosmetic Ingredient Dictionary and Handbook, 11th edition, Jan. 2006, vol. 1, p. 112, CTFA, XP002725309.

* cited by examiner

*Primary Examiner* — Johann R Richter
*Assistant Examiner* — Yanzhi Zhang
(74) *Attorney, Agent, or Firm* — Hamre, Schumann, Mueller & Larson, P.C.

(57) ABSTRACT

The present invention relates to a method of cosmetic care that consists of applying, on at least one area of the body, a cosmetic composition containing an elastic mixture consisting of at least one starch, at least one polymer selected from polyvinyl alcohols, vinylpyrrolidone polymers and copolymers and latex, at least one polyol, and optionally water. The mixture imparts elasticity to the cosmetic product applied on the surface of the skin naturally subjected to deformations, such as the changes of facial expression, pressure of the fingers by contact, or contact with clothing.

6 Claims, 1 Drawing Sheet

COSMETIC CARE COMPOSITION AND METHOD USING AN ELASTIC MIXTURE

BACKGROUND

The present invention relates to a method of cosmetic care that consists of applying, on the skin, a composition comprising a mixture able to form an elastic film. The invention also relates to a particular composition containing this elastic mixture. The composition is of good durability on the skin, and provides a film that is comfortable, flexible and elastic. The composition provides a skin-tightening effect, and deforms elastically to follow the movements and the mechanical deformations of the skin, notably the skin of the face.

The applicant described, in application WO 2003/017967, a mixture for tightening the surface of the skin comprising 10 to 80 wt % of an alginate, from 15 to 75 wt % of a sugar such as sorbitol, and from 3 to 15 wt % of polyvinyl alcohol or polyvinylpyrrolidone. The addition of polyvinyl alcohol or polyvinylpyrrolidone to mixtures containing a polysaccharide and a sugar makes it possible to improve the properties of adhesion to the skin. Moreover, addition of cellulose to this ternary mixture makes it possible to avoid any sensation of pulling of the skin, by imparting elasticity to the polymer matrix formed after application of the composition on the skin, yet without causing sag.

It was found, quite unexpectedly, in the context of a new study, that the addition of starch or of a derivative thereof to a plasticized polymer film can endow it with great elasticity, and that such a mixture may be incorporated in a cosmetic composition that remains stable and homogeneous. The films obtained from this mixture have elasticity at least ten times greater than that of the skin-tightening mixture described in application WO 2003/017967.

SUMMARY OF THE INVENTION

The present invention thus provides a new method of cosmetic care that consists of applying on a part of the body, notably the skin of the face or the cleavage, a cosmetic product comprising a mixture of excipients that imparts elasticity to the skin that is naturally subject to deformations, such as changes of facial expression or contact with clothing or the hands. This mixture of excipients advantageously makes it possible to obtain, on the area of the body in question, in certain embodiments, a transparent film that is soft to the touch, of good durability over time and without being too sticky. Moreover, the film is able to deform reversibly, so that after deformation, for example after stretching, it regains the state that it had before application of the mechanical stress supplied for example by deformation of the skin. The film formed by the composition comprising said mixture has a greater breaking strength, which allows the mechanical properties of the film formed on the surface of the skin to remain intact after application and optional drying of the composition.

The invention therefore relates to a method of cosmetic care that consists of applying, on at least one part of the body, a cosmetic composition containing water and a mixture able to form an elastic film consisting of
  at least one starch advantageously having a gelling or thickening action,
  at least one polymer selected from polyvinyl alcohols, vinylpyrrolidone polymers and copolymers and latex, and
  at least one polyol, and
  optionally water.

"Starch" means, in the sense of the invention, a native starch or a starch derivative, notably a starch hydrolyzing agent.

The method of the invention is advantageously characterized in that said composition is applied on at least one area of skin, in particular the skin of the face or cleavage, that shows signs of aging or tiredness such as loss of firmness, loss of elasticity or skin sag, to obtain an effect selected from a smoothing effect, a lifting effect, an effect of plumpness of the skin, or a combination of two or more of these effects.

The invention also relates to a cosmetic composition containing a mixture able to form an elastic film consisting of at least one starch hydrolyzate, at least one polyol, at least one polymer selected from polyvinyl alcohols, vinylpyrrolidone polymers and copolymers and latex, and optionally water.

The composition of the invention is advantageously free from cellulose derivatives, such as hydroxypropylcellulose, hydroxymethylcellulose, hydroxyethylcellulose, hydroxypropylmethylcellulose or carboxymethylcellulose. The composition of the invention may be free from a weak acid with pKa above 2. The composition preferably contains less than 1 wt % of a lower alcohol such as ethanol or isopropanol.

DETAILED DESCRIPTION

Figure 1:
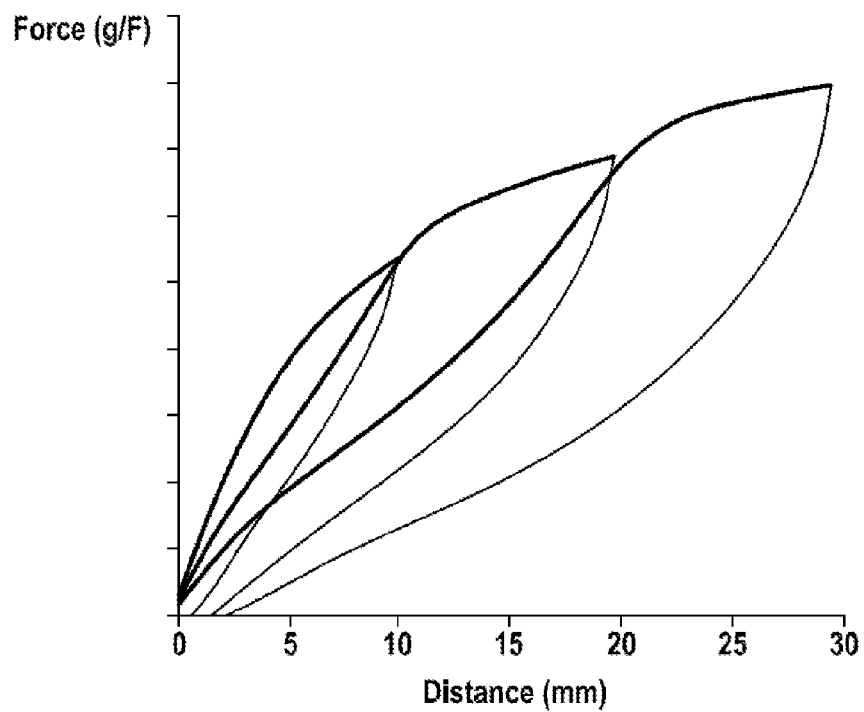
FIG. 1 and FIG. 2 are graphs showing the relationship between force and stretching distance exhibited by film specimens subjected to tensile testing.

In the description given hereunder, the term "cosmetic composition" refers both to the cosmetic composition according to the invention and to the cosmetic composition used in the method of the invention. In the description, the terms "elastic mixture" or "mixture able to form an elastic film" are used synonymously.

In a particular embodiment, the cosmetic composition contains between 0.2 and 90 wt % of a mixture able to form an elastic film consisting of at least one starch with gelling or thickening action, at least one polyol and at least one polymer selected from polyvinyl alcohols, vinylpyrrolidone polymers and copolymers and latex, in which the starch with gelling or thickening action represents between 10 and 30 wt % dry matter, the polymer represents from 20 to 60 wt % dry matter, and the polyol represents between 20 and 60 wt % dry matter, relative to the weight of the mixture, the sum of these three percentages being equal to 100.

The expression "dry matter" denotes the weight of the compound free from water. The expression "between . . . and . . . " is understood to exclude the limits of the range. The expression "from . . . to . . . " is understood to include the limits of the range.

In the elastic mixture, the starch, the polymer and the polyol are preferably in proportions such that the elasticity of a dry film (free from water), with a thickness between 50 and 1000 microns, obtained from this mixture is characterized by
  an elongation at break, also called percentage strain at break, above 50%, and
  a level of residual strain, measured after pulling at least once, below 15%.

The elasticity of the mixture can be measured by a method that is well known by a person skilled in the art, for example with a texturometer of reference TA XT Plus, by measuring the force exerted by a dry film obtained from the mixture and that is submitted to an imposed-speed tensile test. The thickness of the film selected for performing this measurement is preferably between 50 and 1000 microns, more preferably between 90 and 110 microns.

The chemical nature of the polyol as well as the amounts of polyol and starch are preferably selected so that the mixture provides a pleasant feel, without being too sticky, while ensuring good adhesion on the skin. Depending on the type of cosmetic composition that we wish to prepare, a compromise can be defined between the properties of stickiness and adhesion provided by the mixture, so that the cosmetic product has the expected properties.

According to one embodiment, the elastic mixture consists of at least one starch hydrolyzate, at least one polymer selected from polyvinyl alcohols, vinylpyrrolidone polymers and copolymers and latex, and at least one polyol, and optionally water.

The mixture is advantageously free from an alginate, or any other ingredient that would present a risk of destabilizing the mixture of polymer, polyol and starch.

According to one embodiment, starch represents between 10 and 30%, the polymer represents from 20 to 60%, and the polyol represents between 20 and 60%, these percentages being expressed in dry weight of each of the three ingredients relative to the total weight of the three ingredients, with the sum of these three percentages being equal to 100.

The starch advantageously has thickening or gelling action, in the sense that it is likely to produce viscous colloidal solutions, suspensions or gels in water or in an aqueous phase.

"Starch" means, in the sense of the invention, a native starch or a starch derivative, notably a starch hydrolyzing agent. "Native" starch means a starch that has not undergone modification of its chemical structure. Starch "derivative" means a native starch that has undergone chemical, enzymatic or thermal treatments, and has gelling and thickening properties. For example, the starch derivative with the INCI name Aluminum Starch Octenyl Succinate is not a starch that causes gelling or thickening of water. This starch derivative is generally used in cosmetic compositions as an absorbent of oil or of sebum, or as antiperspirant. Moreover, the starches generally used as filler in cosmetic compositions are not starches with gelling action in the sense of the present invention, as they are not present in an aqueous phase and do not interact with the water present in the composition for gelling or thickening the latter. Moreover, esterified corn starch (Dry Flow Plus®) is not a starch with gelling or thickening action.

The starches may undergo chemical modifications, for example acetylation, to an extent such that the gelling and thickening properties of the starch are preserved.

The starches used in the context of the present invention have the advantage of providing a mixture with the aforementioned excipients of the elastic dry films that are transparent and that remain transparent after stretching operation(s) when they are prepared in the form of thin films (typically with thicknesses less than a millimeter). With polymers other than starch, the dry film may be elastic and transparent but may lose its transparency after undergoing mechanical deformations. It is particularly advantageous in the context of the present invention that the film formed on the skin by the mixture remains transparent under the effect of multiple mechanical stresses, so that the color of the deposit of the cosmetic composition containing the mixture, on the skin, is not affected over time.

The starch may be selected from starch hydrolyzates, corn starches, pea starches, tapioca starches, potato starches, rice starches, cassava starches and wheat starches.

The starch is preferably selected from the native starches of maize, potato, pea, tapioca, rice, cassava and wheat. The starch may have the CAS number 9005-25-8.

Among the other starches usable in the context of the present invention, we may mention starch hydrolyzates, oxidized starches, starch phosphates optionally acetylated, starch phosphates optionally phosphated or acetylated, hydroxypropylated starches and hydroxypropylated distarch phosphates.

Among the starch hydrolyzates, we may mention dextrins and maltodextrins. The dextrins may have the CAS number 9004-53-9.

The starch hydrolyzates are classified according to their supply of dextrose, also called dextrose equivalent DE. DE is the number of grams of reducing sugars (regarded as dextrose) per 100 g of dry matter of the product. The dextrins in the sense of the invention are starch hydrolyzates whose DE is notably between 1 and 13, and the maltodextrins are starch hydrolyzates whose DE is notably between 3 and 20.

The dextrins and maltodextrins used according to the invention may be obtained by partial acid and/or enzymatic hydrolysis of a native starch. Various methods of hydrolysis are known. The starch undergoing hydrolysis may be derived from various sources but preferably from maize, potato, tapioca, rice or cassava.

The dextrins or maltodextrins usable according to the invention are in the form of white, yellow or brown powder or a concentrated aqueous solution.

The starch preferably represents from 5 to 30 wt % dry matter, preferably from 10 to 30 wt % dry matter, preferably from 15 to 25 wt % dry matter, relative to the total weight of the mixture.

The polymer advantageously represents from 20 to 60 wt % of the mixture. According to a preferred embodiment, the polymer is a polyvinyl alcohol.

A polyvinyl alcohol comprises —($CH_2$—CHOH)— units and optionally —($CH_2$—CH($OCOCH_3$))— units in a maximum amount of 5 mol % relative to the final polymer.

Preferably, the —($CH_2$—CH($OCOCH_3$))— units are present in the polymer in an amount from 0 to 3 mol %, notably in an amount from 0.05 to 2 mol %. An amount of 5 mol % of —($CH_2$—CH($OCOCH_3$))— units relative to the final polymer corresponds to a degree of hydrolysis of the polyvinyl alcohol of 95%.

Preferably, the polyvinyl alcohol has a weight-average molecular weight (Mw) between 30 000 and 500 000 g/mol, notably from 50 to 200 000 g/mol, and better still from 80 000 to 150 000 g/mol.

As polyvinyl alcohol usable according to the invention, we may notably mention those sold under the names CELVOL®, and more particularly CELVOL® 523.

Preferably, the polymer may be present in the mixture in an amount from 10 to 60 wt %, preferably from 30 to 50 wt %, more preferably from 35 to 45 wt %, relative to the total weight of the mixture.

The polyol advantageously has a low molecular weight, lower than that of the polyvinyl alcohol, for example molecular weight (Mw) less than or equal to 500 g/mol.

The polyols that are particularly preferred are the alcohols having from 1 to 18 carbon atoms and 2 to 6 hydroxyl functions, notably those having from 2 to 12 carbon atoms and/or 2 to 4 hydroxyl functions.

The polyol may be selected from the sugars and derivatives thereof, in particular their esters or their ethers. The sugar is for example selected from the $C_6$ sugars and the $C_{12}$ sugars. A $C_6$ sugar may be glucose, sorbitol, mannitol or galactitol. A $C_{12}$ sugar may be sucrose or lactitol.

The polyol may be selected from the polyalkylene-glycols, notably the poly($C_2$-$C_5$ oxyalkylene)s and more particularly a poly(ethylene oxide) and/or a poly(propylene oxide).

The polyol is preferably selected from glycerol, sorbitol and the glycols. According to an advantageous embodiment, the polyol is glycerol.

The nature of the polyol and its amount will preferably be selected in such a way that the polyol causes the starch to swell. Advantageously, the polyol aids dispersion and plasticizes the polymer.

The weight ratio of polymer to polyol is preferably between 30/70 and 70/30, preferably between 40/60 and 60/40, and more preferably between 45/55 and 55/45.

The polyol may be present in the mixture preferably at a rate from 20 to 60 wt %, preferably at a rate from 30 to 50 wt %, notably at a rate from 35 to 45 wt %, relative to the total weight of the mixture.

According to one embodiment,
the starch with gelling or thickening action represents between 10 and 30%, preferably from 10 to 20%,
the polymer represents from 20 to 60%, preferably from 35 to 45%, and
the polyol represents between 20 and 60%, preferably from 35 to 45%,
these percentages being expressed in dry weight of each of the three ingredients relative to the total weight of the three ingredients, with the sum of these three percentages being equal to 100.

The preferred elastic mixtures used in the method or composition of the invention consist of glycerol, polyvinyl alcohol and dextrin in the following proportions
from 10 to 30 wt %, preferably from 10 to 20 wt %, of dextrin,
from 20 to 60 wt %, preferably from 35 to 45 wt %, of polyvinyl alcohol,
from 20 to 60 wt %, preferably from 35 to 45 wt %, of glycerol,
these percentages being expressed in dry weight of each of the three ingredients relative to the total weight of the three ingredients, with the sum of these three percentages being equal to 100.

The elastic mixture may allow a film to be obtained having a percentage elongation at break above about 50%, preferably above 100%, more preferably above 200% and even more preferably above 250%. The level of residual strain of a film of the elastic mixture is advantageously below 15%.

The percentage elongation at break and the level of residual strain are preferably measured on the mixture described above that is in the form of a film, preferably of rectangular or square shape, and preferably with a thickness equal to at least 100 microns, and which may be up to 1000 microns.

The percentage elongation at break and the level of residual strain are preferably measured by tensile testing of a specimen of the dry mixture.

The tensile test consists of applying two opposite forces on the specimen. The ends of a specimen of film are clamped between two jaws of the tensile tester, one being fixed and the other being integral with a pneumatic piston. The specimen is then submitted to imposed-speed uniaxial stretching over a given distance. The forces are recorded by the force sensor situated on the fixed part of the machine, and a diagram is plotted, reproducing the force exerted by the specimen as a function of specimen elongation, as well as a diagram reproducing the force exerted by the specimen as a function of time.

The level of residual strain is preferably measured after at least one stage of tensile testing, at an imposed distance equal to a third of the specimen length, for example at a distance ranging from one third to four times its length. It is also possible to perform successive cycles of stretching, gradually increasing the stretching distance.

Such a film is essentially anhydrous, i.e. it comprises less than 5 wt % of water.

Such an essentially anhydrous film comprises at least 80 wt % of the mixture, the balance consisting of one or more additives and residual water.

"Essentially anhydrous film" means a film comprising less than 5 wt % of residual water.

The additives may be for example colorants or perfumes.

These elastic films may be used for example as support for temporary tattoos or transfers, the pattern of which, fixed beforehand on the film, is transferred onto the skin by application of the film comprising the pattern.

In this application, the substrate, for example the skin, can have been wetted beforehand with water to facilitate transfer. The film is obtained by spreading an aqueous composition comprising the elastic mixture on a support and optional additives, then drying. Spreading is advantageously performed in such a way that the film has a thickness after drying that is identical over its whole area.

The invention further relates to use of the mixture that has just been described for imparting elastic properties to a cosmetic composition.

According to a preferred embodiment of the invention, the mixture of the invention is incorporated in said cosmetic composition at a concentration between 0.2 and 90%.

The mixture of the invention is incorporated in said cosmetic composition at a concentration ranging for example from 0.4 to 85 wt %, preferably from 1 to 80 wt % relative to the total weight of said composition. According to one embodiment, the mixture of the invention is incorporated in said cosmetic composition at a concentration in the range from 3 to 70 wt %, for example from 5 to 50 wt % relative to the total weight of said composition.

According to another embodiment, the mixture of the invention is incorporated in said cosmetic composition at a concentration in the range from 10 to 40 wt %, or even from 20 to 30 wt % relative to the total weight of said composition.

In a particular embodiment, the composition is in the form of an oil-in-water emulsion containing from 5 to 10 wt % of the elastic mixture, relative to the total weight of said composition.

The amount of the mixture added to the cosmetic composition is advantageously selected as a function of the cosmetic effect required and of the viscosity of the product obtained.

The amount of the mixture is notably selected to allow, at the moment of application of the composition on the skin, the formation of an elastic film during drying of said composition.

The viscosity of the product must be compatible with uniform, pleasant and sufficient application on the skin.

The proportions of the various constituents will be optimized for good viscoelasticity and good adherence on the skin. Depending on the formulations, for example whether it is a foundation or a serum, a compromise will be sought between adherence on the skin and the viscoelasticity of the composition.

For example, if the formulation contains powders, the amount of polyol to add will be greater, in order to maintain plasticity and elasticity.

The cosmetic composition may contain at least one polymer selected from polyvinyl alcohols, vinylpyrrolidone polymers and copolymers and latex, the polymer being in a proportion by weight preferably between 0.02 and 55%, for example between 0.05 and 45%, between 0.10 and 40%, between 0.10 and 30%, between 0.5 and 25%, between 1.75 and 12%, between 2 and 7%, between 2.25 and 6.75%, between 2.75 and 5.25%, or between 3 and 3.5% by weight.

The cosmetic composition may contain at least one polyol in a proportion by weight preferably between 0.02 and 55%, for example between 0.07 and 45%, between 0.10 and 40%, between 0.10 and 30%, between 0.5 and 25%, between 1.75 and 20%, between 2 and 15%, between 5 and 15%, or between 10 and 15% by weight.

The cosmetic composition may contain at least one starch in a proportion by weight preferably between 0.01 and 22.5%, for example between 0.03 and 17.5%, between 0.05 and 13.5%, between 0.25 and 10.5%, between 0.75 and 5%, between 0.8 and 4.5%, between 1 and 3.75%, or between 1.25 and 2.25% by weight.

According to one embodiment, the starch represents from 0.05 to 5 wt % dry matter of the weight of the composition, the polymer represents from 0.1 to 10 wt % of the weight of the composition, and the polyol represents from 0.1 to 10 wt % of the weight of the composition.

The cosmetic composition may further comprise an aqueous phase, which may comprise, besides water, a floral water such as cornflower water, a mineral water and/or a thermal water. Preferably, the composition comprises from 50 to 99 wt %, preferably from 60 to 90 wt %, and more preferably from 70 to 80 wt % of water or of an aqueous phase, relative to the total weight of the composition.

According to a variant of the invention, said composition is characterized in that it further contains at least one cosmetic active ingredient.

The cosmetic active ingredient may in particular be selected advantageously from a hydrating agent, an anti-wrinkle agent, an antioxidant, an antiradical agent, an agent for repairing the destructive effects of ultraviolet radiation or a slimming agent such as caffeine. The hydrating agent is preferably different from urea.

Thus, according to one of its aspects, the invention relates to a composition containing water, at least one cosmetic active ingredient in proportions ranging from 0.01 to 5 wt %, and from 0.2 to 90 wt % dry matter of the mixture described above.

The invention also relates to a cosmetic composition containing a mixture able to form an elastic film consisting of at least one starch hydrolyzate, at least one polyol, at least one polymer selected from polyvinyl alcohols, vinylpyrrolidone polymers and copolymers and latex, and optionally water.

In the description given hereunder, the term "cosmetic composition" refers both to the cosmetic composition according to the invention and to the cosmetic composition used in the method of the invention.

In the composition, the starch, for example starch hydrolyzate, advantageously represents from 0.05 to 5 wt % of the weight of the composition, the polymer, for example polyvinyl alcohol, preferably represents from 0.1 to 10 wt % of the weight of the composition, and the polyol preferably represents from 0.1 to 10 wt % of the weight of the composition.

According to a preferred embodiment of this variant of the invention, said composition is characterized in that it further contains a perfume, a cosmetically acceptable colorant and/or an agent protecting against UVA and UVB ultraviolet radiation, notably a filter or a nano-pigment, such as an oxide of zinc or of titanium.

According to various particular embodiments, the cosmetic composition may be in the form of a gel, a lotion, a serum, a suspension, an oil-in-water emulsion, a water-in-oil emulsion, or a mask.

According to a first embodiment, after spreading on a flat surface and gradual evaporation of the water from the composition, the composition forms a film comprising cosmetic active ingredients, which has mechanical properties of the elastic type and properties of adhesion on the skin.

Such a film is advantageously essentially anhydrous, i.e. advantageously it comprises less than 5 wt % of residual water, preferably less than 2 wt % of residual water.

According to this particular embodiment, the composition may be an anhydrous care mask (containing less than 1 to 3 wt % of water) suitable for application on the skin of the body.

Such a mask is in the form of a film that can be manipulated with the fingers or even trimmed before it is applied on the skin. The film may then be prepared by dissolving the polymer, polyol and starch in water, and optionally adding cosmetic active ingredients or cosmetic additives (colorants, perfumes, etc.).

The film thus obtained may advantageously be cut into strips or into shapes suitable for application on the skin of the body, for example the cleavage, or on a part or the whole of the face.

A care mask may thus be applied on the skin for a sufficient time for the cosmetic active ingredients to diffuse from the film to the layers of the skin.

In these applications, the thickness of the film is of the order of 500 microns to 1 mm, compatible with manual stretching of the film with a view to application thereof on the skin of the body, for example the cleavage, and/or the face.

According to another alternative, the composition is an elastic film essentially free from water comprising at least 80 wt % of the mixture of excipients mentioned above, the balance consisting of cosmetic active ingredients and optionally cosmetic excipients.

Advantageously the film prepared by drying an aqueous composition comprising the mixture described above, at least one cosmetic agent and optionally other cosmetic excipients.

The term "essentially free from water" signifies that the dry film comprises less than 5 wt % of water, preferably less than 2 wt % of residual water.

The film is advantageously prepared by spreading said aqueous composition on a suitable plate, then drying said composition, advantageously by induction.

The film thus obtained may be cut into strips or into shapes suitable for application on the skin of the body, for example the cleavage, or on a part or the whole of the face.

According to another embodiment, the composition is a cosmetic composition applied directly on the skin, which, after application and gradual evaporation of the water from the composition, forms on said skin a film that has mechanical properties of the elastic type with a texture that is particularly suitable for makeup. Moreover, this type of texture has useful properties both esthetically and from the standpoint of comfort of use, notably near areas that are very mobile, for example the eyes and the lips.

The elastic properties of the cosmetic composition are particularly useful for application on areas of the body where there is considerable movement, such as the skin of the face.

The invention further relates to the method of preparing the composition described above.

According to a first embodiment, the method of preparing the composition comprises:
- a first step in which the mixture able to form an elastic film is prepared first by dissolving the polyol in water, then the polymer in water, then the starch with gelling or thickening action in water,
- a second step in which the mixture obtained in the first step is dispersed in an aqueous phase comprising cosmetic excipients.

The elastic mixture may be prepared first by dissolving the polyol, preferably glycerol, in water. The polymer is then dissolved or dispersed in the preceding mixture, with optional supply of heat and stirring. Once the polymer is dissolved or dispersed, the starch is added and preferably stirring is carried out at a temperature above 60° C., for example of the order of 70 to 80° C. for thoroughly homogenizing the ingredients with one another.

According to a second step, the mixture thus prepared in water is added to an aqueous phase comprising cosmetic active agents and/or other cosmetic excipients.

According to another embodiment, the composition is prepared by successively adding each of the components of the mixture directly to the aqueous phase of the cosmetic composition heated to the appropriate temperature, without prior mixing.

In the particular case of an emulsion, the components of the mixture are added to the aqueous dispersing phase before dispersion of the fatty phase.

According to a variant of the method of the invention, the elastic mixture described above is dispersed extemporaneously in a cosmetic base containing water, such as a cream or a serum. The composition is then applied on the skin. The invention also relates to a kit containing the elastic mixture described above, and a cosmetic base, packaged separately.

The invention also relates to the use of a starch hydrolyzate for increasing the elasticity of a plasticized film of polyvinyl alcohol. In particular the starch improves the elasticity, durability and comfort of the cosmetic composition on keratin materials.

According to another of its aspects, the invention relates to the use of the mixture as defined above for preparing a cosmetic composition to form an elastic film on the skin, providing an effect of tightening of the skin after the composition has dried.

According to another of its aspects, the invention relates to a method of cosmetic care that consists of applying, on at least one part of the body, a cosmetic composition containing water and a mixture able to form an elastic film consisting of at least one starch with gelling or thickening action, at least one polymer selected from polyvinyl alcohols, vinylpyrrolidone polymers and copolymers and latex, and at least one polyol, the mixture being such that
- the starch represents between 10 and 30 wt % dry matter,
- the polymer represents from 20 to 60 wt % dry matter, and
- the polyol represents between 20 and 60 wt % dry matter, relative to the weight of the mixture, the sum of these three percentages being equal to 100.

The characteristics that were described above in relation to the cosmetic composition apply to the method of the invention.

According to the method of cosmetic care of the invention, the composition may be applied on at least one area of skin, in particular the skin of the face or cleavage, showing signs of aging or tiredness such as loss of firmness, loss of elasticity, or skin sag, to obtain an effect selected from a smoothing effect, a lifting effect, an effect of plumpness of the skin, or a combination of two or more of these effects.

The method of cosmetic care may comprise topical application of an effective amount of a cosmetic composition as defined above on the areas of the skin in question, to obtain a sensation of second skin.

In the examples, all the percentages are given by weight, the temperature is the ambient temperature, the temperature is given in degrees Celsius and the pressure is atmospheric pressure, unless stated otherwise.

Example 1: Measurements of Elasticity of the Elastic Mixture Used in the Method of the Invention Films were prepared consisting of an elastic mixture according to the invention as well as a skin-tightening mixture described in application WO 2003/017967. Their composition is given in percentages by weight of the ingredients denoted by their INCI name.

| Comparative skin-tightening mixture INCI or chemical name | |
|---|---|
| Sorbitol | 56.1 |
| Algin | 28.0 |
| Polyvinyl alcohol | 11.3 |
| Cellulose gum | 4.6 |
| Elastic mixture INCI or chemical name | |
| Glycerol | 40 |
| Dextrin | 20 |
| Polyvinyl alcohol (PVA) | 40 |

Preparation of the Specimens:

An aqueous solution was prepared containing 8% of the elastic mixture, following the protocol given below.

The water and the glycerol were mixed at 25° C. in a Rayneri (deflocculating) stirrer, then the starch was added as a fine sprinkling. The intermediate mixture thus obtained was stirred quite vigorously in the Rayneri with the aim of creating a vortex, at a temperature of 70-80° C. of the water bath.

The PVA was then added as a fine sprinkling, still with stirring, at 70° C. The whole was mixed for 30 minutes with stirring. If the mixture contained bubbles, it was centrifuged at 2000 rev/min for 15 min.

An aqueous solution was prepared containing 8% of the comparative skin-tightening mixture following the teaching of application WO 2003/017967.

Each solution was spread on a PMMA plate with a spreader bar calibrated for obtaining a film of controlled thickness of 700 μm. The films were left to dry, for the water that they contain to evaporate.

Rectangular test specimens, 50 mm long and 30 mm wide, were cut out.

Tensile Testing

The mechanical properties of the dried test specimens were evaluated using a tensile tester of reference Texturometer TA XT® Plus.

The apparatus was calibrated for distance and force before performing the measurements. For this, the gap between the two jaws was set at 30 mm, and the pretension of the specimens was imposed with an initial pulling force of 20 g, to compensate the elongation of the film due to clamping of the latter in the jaws.

The specimens were subjected to uniaxial tension (constant speed of 1 mm/s). The information supplied by the recorder was the force exerted by the specimen expressed in newtons and the elongation of the specimen in millimeters. The apparatus recorded the force exerted by the specimen as a function of its stretching as well as the force exerted by the specimen as a function of time.

Based on this information, the following were calculated:
1. the percentage strain of the film at the point of rupture, equal to the ratio of the specimen length at the point of rupture to the specimen length before any tension (specimen length means the distance between the jaws), and
2. percentage permanent set (which may also be called final or residual) of the specimen after several cycles of stretching, expressed as ratio of i) the difference between specimen length after stretching and the initial length, to ii) the initial length.

The following cycles of stretching may be carried out:
a) three cycles of stretching each corresponding to tension of 10 mm followed by return to 0 mm, then three cycles of 20 mm, then three cycles of 30 mm, or
b) two cycles of 60 mm, two cycles of 90 mm, then two cycles of 120 mm,
c) two cycles of 120 mm, or
d) a combination of sequences a and b, or
e) a combination of sequences a and c.

"Cycle" means stretching of the specimen at the imposed speed, followed by return to the initial position at the same speed.

The initial distance between the jaws is equal to 30 mm.

Two specimens were submitted to tensile testing successively to verify the reproducibility of the results, applying stretching sequence a).

The residual strain of the elastic mixture is equal to 9-10% after three stretchings of 10 mm, followed by three stretchings of 20 mm, followed by three stretchings of 30 mm. This value was measured from the curves recorded by the texturometer and shown in FIG. 1. The curves corresponding to each of the cycles are superposed, which clearly demonstrates the elastic character of the mixture.

| Percentage elongation of the film at the point of rupture | |
|---|---|
| Elastic mixture | 283% (elongation at break 85 mm/initial length 30 mm) |
| Comparative tightening mixture | 23% (7 mm/30 mm) |

Figure 2:
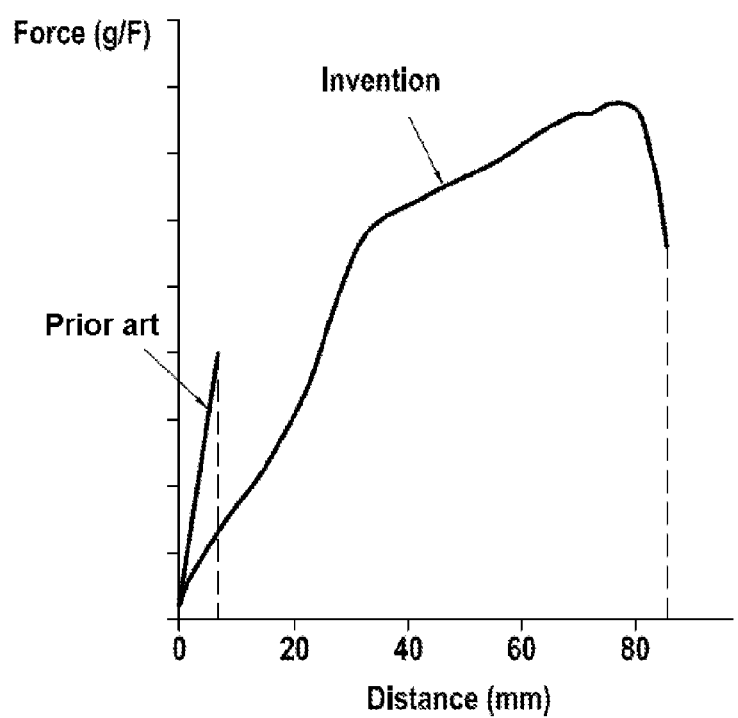

The curves recorded by the apparatus for each of the two mixtures are shown in FIG. 2.

Example 2: Day Creams Containing an Elastic Mixture

The following four compositions of creams were prepared.

| INCI or chemical name | Example 2A wt % | Phase | Example 2B wt % | Phase | Comparative example 1 |
|---|---|---|---|---|---|
| Purified water | q.s. 100 | A | q.s. 100 | A | |
| Isostearyl Isostearate | 4 | C | 4 | C | 4 |
| Polyglycerol-3 | 3 | A | 3 | A | 3 |
| Butylene Glycol | 3 | A | 3 | A | 3 |
| Pentylene Glycol | 3 | A | 3 | A | 3 |
| Phenoxyethanol | 0.7 | A | 0.7 | A | 0.7 |
| Decyloxazolidinone | 0.5 | C | 0.5 | C | 0.5 |
| Acrylates/C10-30 Alkyl Acrylate Crosspolymer | 0.4 | B | 0.4 | B | 0.4 |
| Tetrasodium EDTA | 0.2 | D | 0.2 | D | 0.2 |
| Sodium Hydroxide | <0.1 | D | 0.1 | D | 0.1 |
| Purified water | 2.8 | D | 2.8 | D | |
| Sodium Hyaluronate | <0.1 | B | <0.1 | B | <0.1 |
| Purified water | 5 | E | | | |
| Methyl Gluceth-20 | | | 1.8 | E | 1.8 |
| Gelling complex[2] | | | 7 | F | |
| Starch[1] | 1.5 | B | 1.5 | B | |
| Glycerol | 3 | A | 3 | A | 3 |
| Polyvinyl Alcohol | 3.2 | | 3.2 | | <0.1 |

[1]STARCH = Dextrin or native wheat starch or native corn starch
[2]Gelling complex: sorbitol/cellulose gum/polyvinyl alcohol/Algin/water, described in the example in application WO 2003/017967

Examples 2A and 2B were prepared as follows:

Mix phase A under Ystral, and heat to 80° C. Add the polyvinyl alcohol to phase A. Add phase B to phase A under Ystral. Prepare phase C on a water bath and add it to phase A. Prepare phase D on a water bath and add it to phase A. Add phase E, then phase F if applicable.

Comparative example 1 corresponds to a composition containing the mixture described in application WO 2003/017967.

The biomechanical properties of the skin of a person on which one of these compositions had been applied were evaluated with a Cutometer of reference CUTOMETER SEM575 from the company Courage & Khazaka, with a probe diameter of 2 mm. More precisely, the residual strain of an area of the skin when the surface of the latter is aspirated into a cylindrical chamber was measured. The strain was measured before and after application of each of the three compositions on the skin, to verify their elastic character.

The method consisted more precisely of creating a perpendicular partial vacuum (ranging from 20 to 500 mbar) in a small cylindrical chamber affixed on the skin and measuring the displacement of the skin within the chamber over time starting from the moment when the partial vacuum was applied and after breaking the vacuum.

The raising of the surface of the skin was measured with an integrated optical measurement system, made up of a light emitter and receiver.

The strain curve, called "rheogram", of the elongation of the skin (in mm) was plotted as a function of time. Time zero corresponded to application of the partial vacuum (Luis Rodrigues, EEMCO Guidance to the in vivo Assessment of Tensile Functional Properties of the skin, Part 2: Instrumentation and Test Modes, Skin Pharmacol Appl Skin Physiol 2001; 14: 52-67).

The measurements were performed on the forearm, 8 cm from the fold of the elbow, on the anterior face of the forearm.

The cream was applied with a finger stall by the technician in a single application at a rate of 2.0 mg/cm². The temperature for carrying out the measurement was 22° C.±2° C., and the hygrometry was 50%±10%.

In the context of this study, the partial vacuum was selected equal to 300 mbar, and the skin was submitted to three cycles with spacing of 20 minutes for stabilization, each cycle comprising 10 sequences of aspiration (5 seconds) followed by relaxation (1 second). The cream was applied after the first cycle.

The residual strain of the skin was measured at the end of each cycle and it was found that the residual strain of the skin remains stable when the composition is applied according to the method of the invention, whereas this strain increases when a composition of the prior art is applied.

Synoptic Tables of the Results:

| Residual strain | After the first cycle | After the third cycle |
| --- | --- | --- |
| Comparative example 1 | 0.073 | 0.088 |
| Example 2A | 0.075 | 0.076 |
| Example 2B | 0.081 | 0.089 |

The rheology of the elastic mixture, and in particular its elasticity, offers the advantage that it does not vary as a function of temperature, so that the results of the tests that were carried out at 25° C. on apparatus for measurement in tension are in agreement with the tests that were carried out once the mixture was added to a cosmetic product and applied on consumers' skin, the temperature of which is of the order of 33° C.

Example 3: Day Cream Comprising an Elastic Mixture

The cream according to the invention had the following formula. The percentages are by weight.

| INCI name or chemical name | |
| --- | --- |
| STARCH* | 0.3 |
| Polyvinyl alcohol | 0.5 |
| Glycerol | 2.5 |
| GELLING COMPLEX* | 1.0 |
| Methyl methacrylate crosspolymer | 1.5 |
| Tetrasodium EDTA | 0.1 |
| Alkyl methyl silicone | 3.2 |
| Caprylyl glycol | 0.1 |
| Pentylene glycol | 3.0 |
| Sodium hydroxide | 0.1 |
| Carbomer | 0.3 |
| Xanthan gum | 0.1 |
| Steareth-2 | 0.9 |
| Steareth-21 | 2.1 |
| C16-C22 fatty alcohols | 1.6 |
| Polyethylene | 2.6 |
| Cetearyl isononanoate | 1.5 |
| Alkyl triglycerides | 5.2 |
| Hydrogenated polyisobutene | 4.0 |
| Dimethicone | 1.4 |
| Phospholipids | 1.0 |
| Decyloxazolidinone | 1.5 |
| Fatty phase gelling polymer | 4.0 |
| Anti-aging cosmetic agents | 2.6 |
| Perfumes | 0.3 |
| Preservatives | 0.7 |
| Purified water | q.s. 100 |

*STARCH = Dextrin or native wheat starch or native corn starch
*GELLING COMPLEX: sorbitol/cellulose gum/polyvinyl alcohol/Algin/water, described in the example in application WO 2003/017967

The cream was applied on the skin in the morning. The deposit formed by the composition after application was invisible owing to the properties of transparency of the film formed by the elastic complex of the invention.

The properties of elasticity and of reversibility of this deposit demonstrated in the foregoing examples provided a smoothing and tightening effect throughout the day despite the movements of the face, and gave the skin a plump appearance.

Example 4: Tightening Serum Comprising an Elastic Mixture

A serum according to the invention had the following formula. The percentages are by weight.

| INCI name or chemical name | |
| --- | --- |
| STARCH* | 0.5 |
| Polyvinyl alcohol | 0.6 |
| Glycerol | 5.5 |
| GELLING COMPLEX* | 5.0 |
| Polysaccharides | 0.1 |
| Esterified jojoba oil | 1.0 |
| Carboxymethyl dextran | 0.7 |
| Acrylate copolymer | 1.1 |
| Tetrasodium EDTA | 0.1 |
| Caprylyl glycol | 0.3 |
| Pentaerythrityl tetraisostearate | 4.0 |
| Sodium hydroxide | 0.1 |
| Ethanol | 2.0 |
| Butylene glycol 1-3 | 2.0 |
| Polymethylsilsesquioxane | 1.0 |
| Cosmetic active ingredients | 12.5 |
| Perfumes | 0.3 |
| Preservatives | 0.5 |
| Purified water | q.s. 100 |

*STARCH = Dextrin or native wheat starch or native corn starch
*GELLING COMPLEX: sorbitol/cellulose gum/polyvinyl alcohol/Algin/water, described in the example in application WO 2003/017967

This serum was applied on areas of skin showing signs of skin aging or sag.

The elastic complex provided the skin with a particularly pleasant feel, whereas the elasticity of the film deposited after application provided a lifting and smoothing effect, particularly prolonged throughout the day, despite the movements of the face.

The invention claimed is:

1. A method of cosmetic care that comprises applying, on at least one part of the body, a cosmetic composition containing water and a mixture, wherein the mixture consists of
   10 to 20 wt % of dextrin,
   35 to 45 wt % of polyvinyl alcohol,
   35 to 45 wt % of glycerol,
   these percentages being expressed in dry weight of each of the three ingredients relative to the total weight of the three ingredients, with the sum of these three percentages being equal to 100.

2. A method as claimed in claim 1, wherein the cosmetic composition is in the form of a gel, a lotion, a serum, a suspension, an oil-in-water emulsion or a water-in-oil emulsion.

3. The method as claimed in claim 1, wherein the cosmetic composition is in the form of an anhydrous care mask containing no more than 3 wt % of water, suitable for application on the skin of the body.

4. The method as claimed in claim 1, wherein said composition is applied on at least one area of skin showing signs of aging or tiredness, to obtain an effect selected from a smoothing effect, a lifting effect, an effect of plumpness of the skin, or a combination of two or more of these effects.

5. The method as claimed in claim 1, wherein the cosmetic composition contains from 0.4 to 85 wt % of the mixture.

6. The method as claimed in claim 4, wherein said composition is applied on at least one selected from skin of the face and skin of the cleavage.

* * * * *